(12) United States Patent
Barve et al.

(10) Patent No.: US 7,128,815 B2
(45) Date of Patent: Oct. 31, 2006

(54) PROCESS FOR RECOVERY OF PURE ACRYLONITRILE

(75) Inventors: Prashant Purushottam Barve, Maharashtra (IN); Shrikant Madhukar Ghike, Maharashtra (IN); Ravindra William Shinde, Maharashtra (IN); Milind Yashwant Gupte, Maharashtra (IN); Chandrashekhar Narayan Joshi, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 373 days.

(21) Appl. No.: 10/395,886

(22) Filed: Mar. 25, 2003

(65) Prior Publication Data

US 2004/0188236 A1  Sep. 30, 2004

(51) Int. Cl.
  *B01D 3/40* (2006.01)
  *C07C 255/08* (2006.01)

(52) U.S. Cl. .......................... 203/64; 203/89; 203/91; 558/466

(58) Field of Classification Search .................... 203/1, 203/2, 14, 89, 91, 63, 64, 100; 558/466
See application file for complete search history.

(56) References Cited

U.S. PATENT DOCUMENTS

| 3,051,630 | A | * | 8/1962 | Hadley et al. | 203/44 |
| 3,257,446 | A | * | 6/1966 | Grice et al. | 558/465 |
| 3,352,764 | A | | 11/1967 | Tyler | |
| 3,635,917 | A | * | 1/1972 | Roth et al. | 523/347 |
| 3,980,529 | A | * | 9/1976 | Wilhelm et al. | 203/89 |
| 4,414,063 | A | * | 11/1983 | Smiley | 203/66 |
| 4,808,344 | A | | 2/1989 | Hallenburg et al. | |
| 6,559,248 | B1 | * | 5/2003 | Hendriksen et al. | 526/77 |

* cited by examiner

*Primary Examiner*—Virginia Manoharan
(74) *Attorney, Agent, or Firm*—Nixon & Vanderhye P.C.

(57) ABSTRACT

Process for recovery of highly pure acrylonitrile by quickly vaporizing under vacuum the contaminated acrylonitrile as well as fresh acrylonitrile followed by contacting with hydrophilic agents in an extractive distillation column using plural number of packed sections.

6 Claims, 3 Drawing Sheets

PROCESS FOR RECOVERY OF PURE ACRYLONITRILE

FIELD OF THE INVENTION

Figure 1:
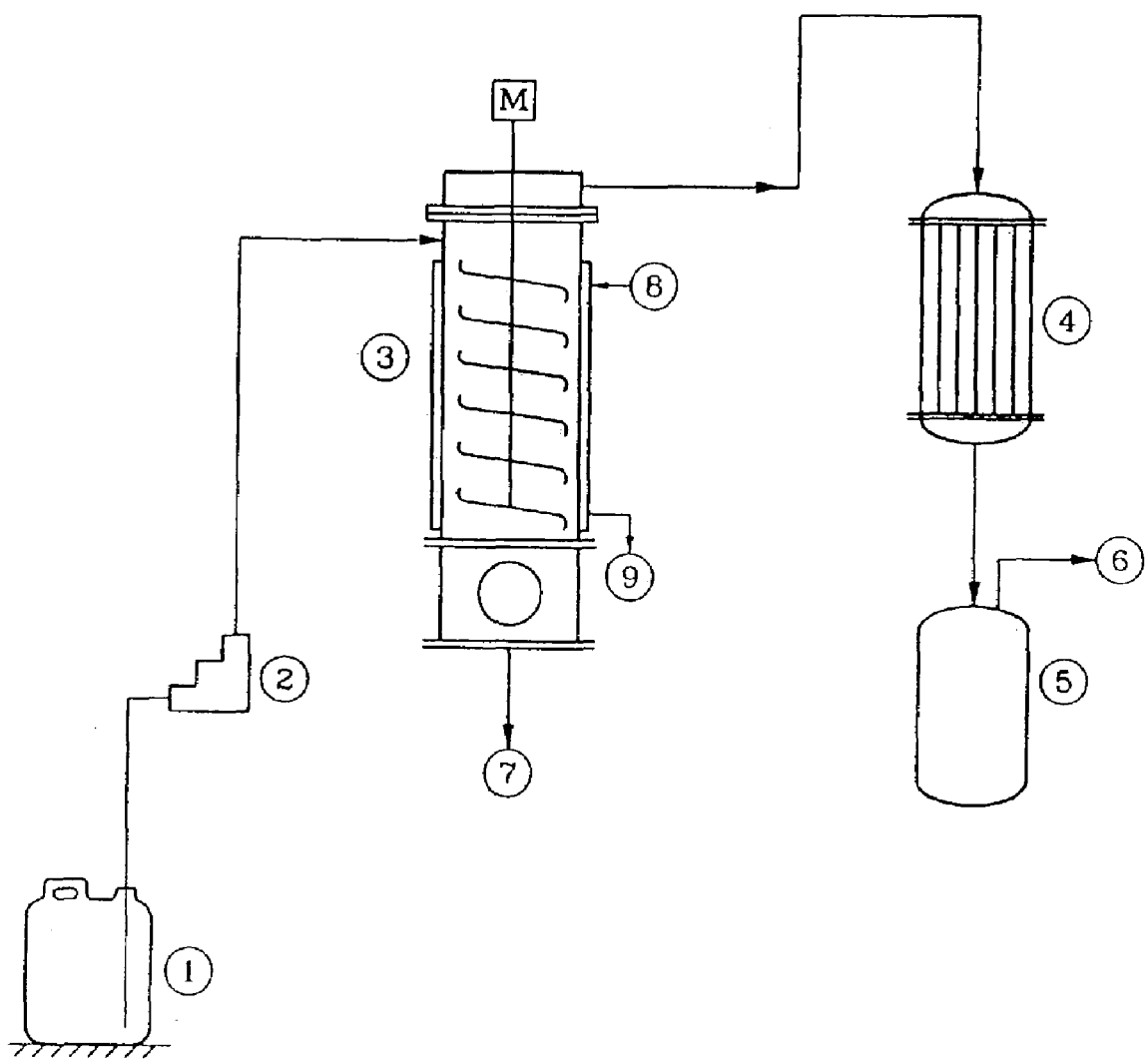

The present invention relates to a process for the recovery of highly pure acrylonitrile. More particularly the present invention relates to a process for the recovery of highly pure acrylonitrile from contaminated acrylonitrile as well as fresh acrylonitrile having 0.5–1% moisture content by quickly vaporization under vacuum followed by contacting with hydrophilic agents in an extractive distillation column using plural number of packed sections.

BACKGROUND OF THE INVENTION

There are many procedures for the production of acrylonitrile. This compound is one of the most important organic chemical intermediates available. It is a major intermediate in the manufacture of a wide range of products, plastics, synthetic rubber, synthetic fibers, soil conditioners and the like. For many uses, acrylonitrile must be of high purity and, for this reason, strict specifications must be met in the commercial manufacture of acrylonitrile. Each of the commercial procedures used for the preparation of acrylonitrile produces its own set of impurities and by-products and each presents its own problems of purification. (See U.S. Pat. No. 3,459,639.)

Different processes for making acrylonitrile result in the formation of different by-product contaminants. Accordingly, different proce dures may be required to remove the contaminants and purify the acrylonitrile. Due to such constraints, any given acrylonitrile purification process is not likely to be universally interchangeable with respect to its usefulness in the purification of all acrylonitrile containing compositions.

As indicated in U.S. Pat. No. 4,404,064, one very good and commercially practiced method of producing olefinically unsaturated nitrites is the catalytic reaction of ammonia and an olefin. For example, acrylonitrile and methacrylonitrile may be produced by the vapor phase catalytic oxidation of propylene and isobutylene respectively, in the presence of ammonia. In these processes, significant amounts of impurities are produced. The production of acrylonitrile from ammonia and propylene results in the formation of significant quantities of acetoni trile., propionitrile, acetone and the like. It is necessary to remove these by-product impurities to produce an unsaturated nitrite suitable for polymerization to other products.

U.S. Pat. No. 3,459,639 to Borrel et al discloses a process for the purification of a complex mixture of acrylonitrile, acetonitrile and other materials formed in the vapor phase conversion of acrolein or propylene to acrylonitrile over a catalyst in the presence of ammonia and oxygen. Separation of acrylonitrile from acetonitrile is accomplished by extractive distillation using deionized water at a pH of at least 5 and preferably 5–7 with the introduction of an alkaline-agent to the distillation mixture.

U.S. Pat. No. 4,377,444 to Wu relates to the recovery and purification of olefinic nitrites and more particularly pertains to an improved process for the recovery and purification of olefinic nitrites, such as methacrylonitrile and acrylonitrile, produced by the ammoxidation of isobutylene and propylene from mixtures of said olefinic nitrites with such materials as acetonitrile, hydrogen cyanide, propionitrile, butyronitrile, methacrolein, acrolein, acetone, acetaldehyde, etc. Wu points out that when an olefin, such as isobutylene or propylene, is allowed to react with ammonia and molecular oxygen in the vapor phase at elevated temperatures and in the presence of an ammoxidation catalyst, the corresponding olefinic nitrites, such as methacrylonitrile and acrylonitrile, are produced along with varying amounts of by-products of the ammoxidation reaction including acetonitrile, hydrogen cyanide, propionitrile, butyronitrile, methacrolein, acrolein, acetone, acetaldehyde, and mixtures of the desired olefinic nitrile, and some of these by-products appear in the ammoxidation reactor effluent. In accordance with the Wu process, the products of the ammoxidation reaction are recovered in a first step by absorption in water during which step some heavy or high-boiling organic compounds are formed through polymerization, condensation, etc., of some of the lighter organic products. Accordingly, the Wu process is an improved method for separating the olefinic nitrites from the by-products formed in the ammoxidation reaction as well as from the heavy organic compounds.

The process disclosed in U.S. Pat. No . 3,051,630 to Hadley et al also relates to the purification of acrylonitrile. However, this process is particularly applicable to the purification of acrylonitrile produced by the catalytic vapor phase reaction of acrolein with ammonia and molecular oxygen. In such reactions, the crude acrylonitrile is usually recovered in the form of a dilute aqueous solution, which also contains varying amounts of acrolein and hydrogen cyanide, by contacting the gaseous reaction product with water, preferably after neutralization of any unreacted ammonia.

The processes mentioned above, mostly deal with the purification of acrylonitrile from the impurities formed during the manufacture of acrylonitrile.

The process disclosed in PCT Patent publication number WO 88/01263 to Hallenburg et al [Lubrizol Corp. USA] relates to a process for recovering and purifying unreacted acrylonitrile from contaminants when excess amounts of acrylonitrile are reacted with another reactant to produce a product such as 2-acrylamido-2-methyl propane sulfonic acid. According to this process, the unreacted acrylonitrile containing contaminants such as the residual acids is first neutralized by adding a base such as NaOH, $NH_3$, $Ca(OH)_2$ or lime (i.e., calcium oxide) and/or mixtures thereof which react with contaminant acids present forming various salts, e.g., calcium salts. Hallenburg points out that lime is the preferred base and is used in the presence of a catalytic amount of water. The neutral salts which are formed as solids precipitate out or can be separated away along with any unreacted lime by conventional means. At this point, the acrylonitrile product still contains contaminants, which would interfere with the use of the acrylonitrile in the synthesis of other materials such as 2-acrylamido-2-methyl propane sulfonic acid. Accordingly, after the removal of the neutral salts, the contaminated acrylonitrile is preheated to about 43° C. to 60° C. in a heat exchanger under vacuum. This preheated material is then transferred to a lower portion of a distillation tower. The tower is comprised of a lower opening, a plurality of distillation trays and an upper opening, with the tower being maintained under vac uum. A majority of the heated material entering the distillation tower falls to the bottom of the tower whereas a small amount of purified acrylonitrile rises to the top of the tower and is evacuated therefrom via a pressure differential. The heated material falling to the bottom of the distillation tower is divided into two portions with the major portion being returned to the heat exchanger and a minor portion is transferred to a thin film evaporator which is maintained under vacuum at a temperature above the melting point and below about 78° C. and preferably in the range of about 49° C. to about 63° C. Within the thin film evaporator, contaminated wastes containing relatively high amounts of residual acids fall to the bottom of the evaporator and a partially purified acrylonitrile product is removed from the top of the evaporator and transferred to the distillation tower. A highly purified acrylonitrile product is removed from the top opening of the distillation tower. Contaminants within the distillation tower continue to fall to the bottom of the tower and are removed. The purified acrylonitrile product removed from the upper portions of the distillation tower contains negligible amounts of contaminants such as residual acids and acrylamides.

Although this process is good for recovering and purifying the excess unreacted acrylontrile from the contaminants generated during manufacture of products such as 2-acrylamido-2-methyl propane sulfonic acid, it has following disadvantages.
1. The unreacted acrylonitrile needs to be first neutralized with bases like lime. This invariably generates slurry of the salts of lime in acrylonitrile. The separation of these salts by conventional means like filtration is difficult and needs a special hardware for closed handling to avoid human exposure to acrylonitrile vapors. If settling and decantation method is used, then it can pose the difficulties in disposal of wet cake loaded with hazardous acrylonitrile.
2. For proper neutralization by lime, water in catalytic proportions is essential. This calls for addition of water to acrylonitrile. Thus the acrylonitrile recovered by this method would contain water in dissolved state as per the solubility characteristics. On the other hand, the moisture content of more than 0.2% by weight in acrylonitrile drastically reduces the yield during the process of manufacture of materials such as 2-acrylamido-2-methyl propane sulfonic acid. Therefore this recovered acrylonitrile has to be further dried by a suitable method like adsorption on molecular sieves etc., before it is used as a reactant in the process. Similarly, the commercial grade acrylonitrile also contains about 0.5% [by wt] of moisture. The moisture content has to be reduced to below 0.2% [by wt] by the methods like adsorption on molecular sieves etc., before this acrylonitrile is used for the manufacture of materials such as 2-acrylamido-2-methyl propane sulfonic acid. Such adsorption processes invariably pose the difficulties in disposal of acrylonitrile vapors during the regeneration cycle.
3. In the process disclosed in the above patent, acrylonitrile is continuously in contact with the contaminants either in the heat exchanger or in the thin film evaporator, due to recirculation and longer residence time distributions. This may induce the polymerization of acrylonitrile and so loss of acrylonitrile. Similarly fouling of heat transfer surfaces and equipment also may not be completely avoided.
4. The process needs a separate hardware for minimizing the moisture content in the unreacted acrylonitrile recovered by above method as well as that in the fresh make-up.
5. The longer residence time in the process imposes restriction on operating temperature for preheating and vaporization of contaminated acrylonitrile within a range of 43° C. to 60° C.

In order to synthesize 2-acrylamido-2-methyl propane sulfonic acid, excess amounts of acrylonitrile are combined with sulfuric acid and isobutene. The resulting reaction product includes 2-acrylamido-2-methyl propane sulfonic acid along with substantial amounts of unreacted acrylonitrile and other by-products. The 2-acrylamido-2-methyl propane sulfonic acid can be separated away leaving the acrylonitrile present along with various residual acids, acrylamides, and other by-product contaminants. The contaminants are present in an amount of about 1–2 percent by weight based on the weight of the composition.

The acid contaminants include sulfuric acid, isobutylene monosulfonic acid, isobutyl ene disulfonic acid and small amounts of 2-acrylamido-2-methyl propane sulfonic acid, t-butyl acrylamide and acrylamide. If the acrylonitrile containing the 1 to 2 percent contaminants such as the residual acids is reused for the production of the 2-acrylamido-2-methyl propane sulfonic acid, the resulting product (i.e., the 2-acrylamido-2-methyl propane sulfonic acid) will have various undesirable characteristics. For example, the resulting product will contain undesirable polymerized material formed by the polymerization of acrylonitrile monomers with contaminant monomers. Accordingly, it is desirable to purify the acrylonitrile before it is reused, and the present invention is directed to such a purification process and the product resulting therefrom.

Accordingly, this purified acrylonitrile itself has the desired average molecular weight and excellent storage stability. Further, the purified acrylonitrile can be utilized in the production of other materials such as being recycled for use in the production of 2-acrylamido-2-methyl propane sulfonic acid, which will also have a high degree of purity. This high degree of purity is particularly important to obtain when eliminating contaminants, which are particularly reactive with the acrylonitrile. Such reactive contaminants react with the acrylonitrile to form water insoluble polymers which cloud up aqueous solutions prepared by including 2-acrylamido2-methyl propane sulfonic acid with water.

OBJECTS OF THE INVENTION

The main object of the present invention is to provide a process for recovery of highly pure acrylonitrile by quickly vaporizing the contaminated acrylonitrile as well as fresh acrylonitrile having 0.5–1% moisture content followed by contacting with hydrophilic agents in an extractive distillation column using plural number of packed sections Another object of the present invention is to avoid the neutralization of contaminated acrylonitrile by bases.

Still another object of the present invention is to avoid any additional contamination of water during the recovery process.

Yet another object of the present invention is to minimize the residence time for the preheating and vaporization of contaminated acrylonitrile so that the same can be carried out at higher temperature than 78° C. with minimum loss due to polymerization.

A further another object of the present invention is to provide a method of extractive distillation to reduce the moisture content of acrylonitrile to as low as possible.

SUMMARY OF THE INVENTION

Accordingly the present invention provides a process for the recovery of highly pure acrylonitrile from contaminated acrylonitrile or fresh acrylonitrile hanving 0.5–1% moisture content or a mixture thereof which comprises vaporizing the contaminated acrylonitrile or a or fresh acrylonitrile hanving 0.5–1% moisture content or a mixture thereof in a conventional agitated thin film evaporator (ATFE) running at a speed of 600–1200 rpm, at a temperature of 100–150° C. under reduced pressure of 60–250 mm Hg abs, contacting the above said vapours feed of fresh acrylonitrile or a mixture of contaminated acrylonitrile and fresh acrylonitrile with a hydrophilic agent, condensing the above said distillate by known method to obtain the desired pure acrylonitrile.

In an embodiment of the present the speed of agitated thin film evaporator (ATFE) used is preferably in the range of 700–1000 rpm.

In yet another embodiment the temperature used for vaporising is in the range of 120–140° C.

In yet another embodiment the reduced pressure used is preferably in the range of 100–200 mmHg abs.

In yet another embodiment the hydrophillic agent used is a compound having a diol group, selected from the group consisting of 1,2-Propane Diol, mono ethylene glycol, Di-ethylene glycol and glycerol.

Furthermore the most important feature of the present invention is to provide a process for recovery of highly pure acrylonitrile by quickly vaporizing the contaminated acrylonitrile as well as fresh acrylonitrile followed by contacting with hydrophilic agents in an extractive distillation column using plural number of packed sections

BRIEF DESCRIPTION OF THE ACCOMPANYING DRAWINGS

In the drawing accompanying this specification, FIG. 1 represents the schematic of the pilot plant set-up for the process of recovery of highly pure acrylonitrile by quickly vaporizing under vacuum the contaminated acrylonitrile followed by condensation showing first embodiment of the present invention.

Figure 2:
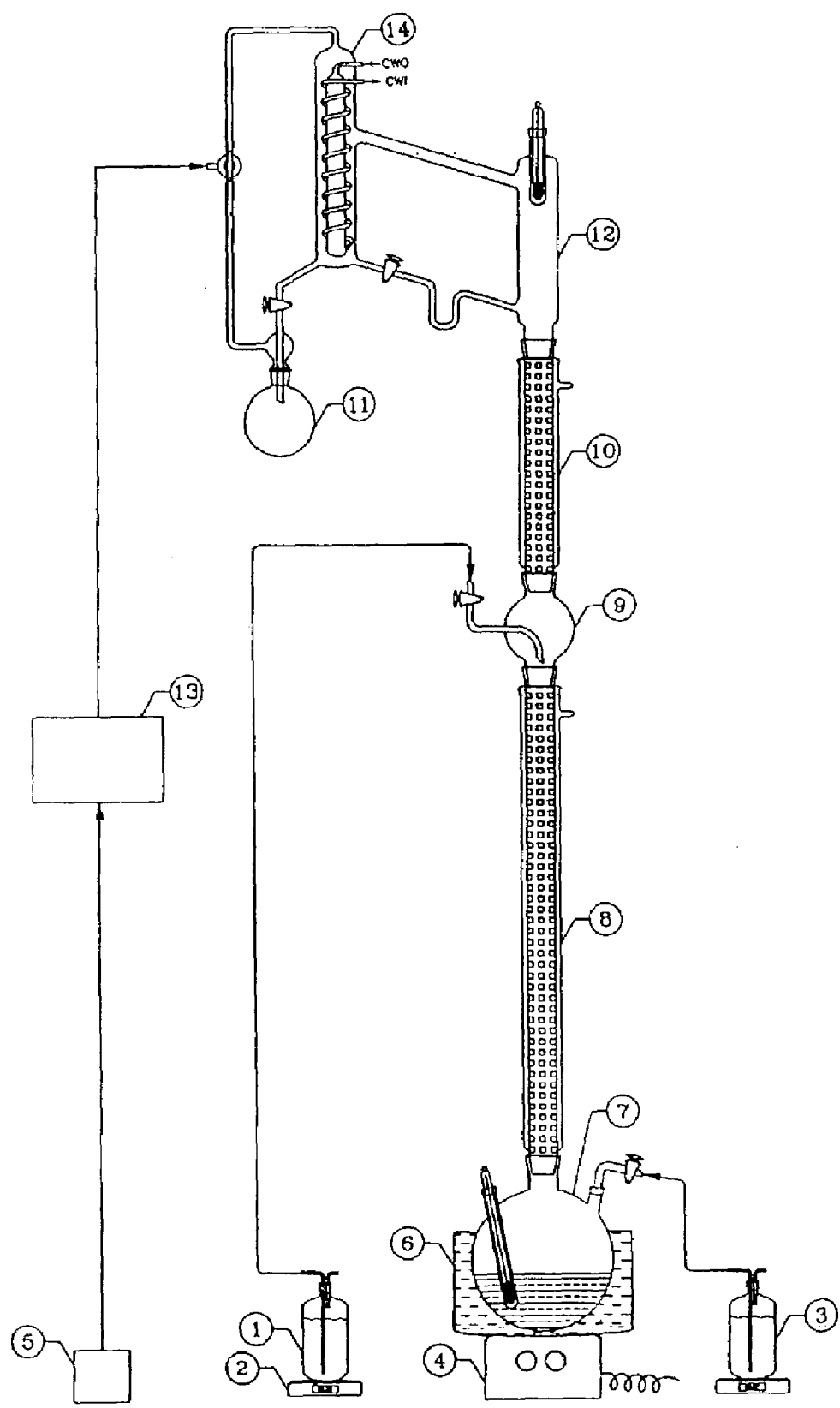

In the drawing accompanying this specification, FIG. 2 represents the schematic of the experimental set-up for the process of recovery of highly pure acrylonitrile by quickly vaporizing the commercial grade fresh acrylonitrile having 0.5–1% moisture content under vacuum followed by contacting with hydrophilic agents in an extractive distillation column using plural number of packed sections showing second embodiment of the present invention.

Figure 3:
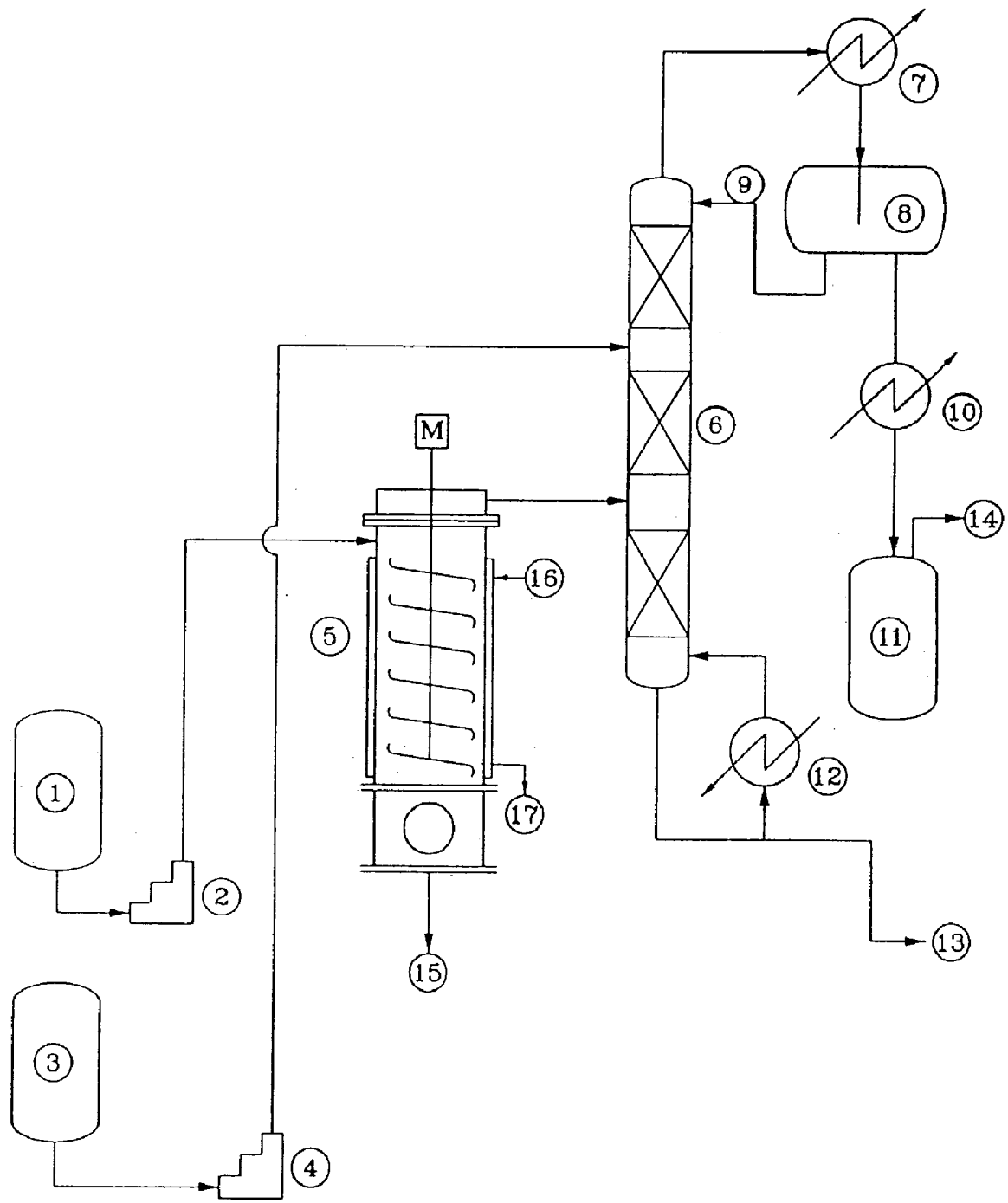

In the drawing accompanying this specification, FIG. 3 represents a schematic view of the conceptual combined purification and recovery system, which can be used, on an industrial scale for the process of recovery of highly pure acrylonitrile by quickly vaporizing under vacuum the combined mixture of contaminated acrylonitrile and commercial grade fresh acrylonitrile having 0.5–1% moisture content and followed by contacting with hydrophilic agents in an extractive distillation column using plural number of packed sections showing third embodiment of the present invention.

DETAILED DESCRIPTION OF THE INVENTION

FIG. 1 is a schematic view of the pilot scale purification system used in a preferred embodiment of the present invention. Contaminated acrylonitrile from the container (1) is fed to the agitated thin film evaporator [ATFE] (3) via metering pump (2). ATFE is provided with 0.12 sq.m area for heat transfer and a jacket for circulation of heating medium through inlet (8) and outlet (9). The agitator in ATFE is run at 1200 rpm. Due to very short residence time in the ATFE, almost pure ACN vaporizes and the vapors are condensed in the down stream condenser (4) of 1 sq.m. area. The condensed and recovered acrylonitrile is collected in the receiver (5), under vacuum (6). The residue (7) from the bottom of the ATFE is collected in a suitable container at the bottom.

FIG. 2 represents the schematic of the experimental set-up used in the second preferred embodiment of the present invention. Fresh acrylonitrile is stored in similarly stored in container (3). A 2 liter capacity three neck round bottom flask (7) immersed in a water bath (6) is heated by a heater (4). The round bottom flask (6) is filled with 600 g of hydrophilic agent and maintained at about 70 to 75° C. The flask (6) is connected to first packed section (8) of a distillation column of 25 mm diameter and 1100 mm height, packed with 10 mm glass bids. The top of this section is connected to a receiver (9) where the hydrophilic agent can be fed via a dip tube from container (1). Container (1) is kept on a weighing scale (2) for cumulative weight measurement. Receiver (9) is further connected to second packed section (10) of the distillation column of 25 mm diameter and 500 mm height, packed with 10 mm glass bids. The distillation column is provided with a condenser (14) via a vapor space (12). The distillate is collected in the receiver (11). Whole set up is maintained under vacuum via the trap (13) and vacuum pump (5). The feeds of moist acrylonitrile from (3) and hydrophilic agent from (1) are sucked into the system due to vacuum. Their feed rate is controlled by the feed valves as shown in the figure.

FIG. 3 shows a schematic view of the conceptual combined purification and recovery system, which can be used, on an industrial scale. Contaminated acrylonitrile may be mixed with fresh acrylonitrile having about 0.5 to 1% moisture content. This combined impure acrylonitrile is stored in container (1). It is fed to the agitated thin film evaporator [ATFE] (5) via metering pump (2). ATFE is provided with adequate area for heat transfer and a jacket for circulation of heating medium with inlet (16) and outlet (17). The agitator in ATFE is run at high rpm. Due to very short residence time in the ATFE, almost pure acrylonitrile along with water vaporizes. The vapors are fed to an extractive distillation column (6). The column is provided with plural number of packed sections. Hydrophilic agent is stored in container (4) from where it is fed to the distillation column (6) at appropriate stage by the pump (4). The overhead vapors from (6) are condensed in the condenser (7). The condensate is collected in the receiver (8), under vacuum (14). Stream (9) provides adequate reflux to (6) while the recovered acrylonitrile is cooled in cooler (10) and collected in the receiver (11). Reboiler (12) caters to the heat requirements of (6). The residue (15) from the bottom of the ATFE is collected in a suitable container at the bottom for conventional treatment and disposal. The bottom stream (13) of the column (6) is sent for recovery of hydrophilic agent in a conventional system.

The ingredients and the process conditions etc. used in the manufacturing method of this invention are described below.

The chemical product 2-acrylamido-2-methyl propane sulfonic acid is used throughout industry for a variety of different purposes. The 2-acrylamido-2-methyl propane sulfonic acid product, as well as other products, can be produced by reacting an excess amount of acrylonitrile with sulfuric acid and isobutylene. Due to economic and environmental factors, it is desirable to reuse the unreacted acrylonitrile in order to produce more 2-acrylamido-2-methyl propane sulfonic acid. However, the unreacted acrylonitrile is present with other contaminants, such as acrylamides and residual acids and as such has poor storage stability and can not be reused in the production of 2-acrylamido-2-methyl propane sulfonic acid of high quality. If the acrylonitrile is not purified to the necessary degree, it will react with contaminants present and form water insoluble compounds. In order to produce a high quality 2-acrylamido-2-methyl propane sulfonic acid product and make efficient use of acrylonitrile, the present inventors have discovered an improved means for the purification of the unreacted contaminated acrylonitrile waste stream generated from the production of 2-acrylamido-2-methyl propane sulfonic acid. When an excess amount of acrylonitrile is used in the production of 2-acrylamido-2-methyl propane sulfonic acid, the desired 2-acrylamido-2-methyl propane sulfonic acid product formed can be removed leaving behind acrylonitrile present with 1–2 percent by weight of contaminants (such as sulfuric acid, isobutylene monosulfonic acid, isobutylene disulfonic acid, acrylamides and small amounts of 2-acrylamido-2-methyl propane sulfonic acid) which were not successfully removed. This acrylonitrile is the contaminated waste stream acrylonitrile referred to above.

The present inventors have found that in order to achieve the objectives as stated above, it is desirable to quickly vaporise the contaminated or fresh acrylonitrile on a hot surface using an equipment like agitated thin film evaporator or a hot bath of inert material followed by extractive distillation in contact with hydrophilic agents.

Now referring to FIG. 1, the contaminated acrylonitrile from (1) is fed to an agitated thin film evaporator [ATFE] (3) by pump (2). The ATFE is maintained at 100° C. to 150° C., preferably in the range of 120° C. to 140° C. by suitable heating medium in its jacket. The agitator of the ATFE is preferably of close clearance type so that the feed is subjected to the hot surface of ATFE in form of a thin film. The speed of agitator is controlled at 600 to 1200 RPM, preferably in the range of 700 to 1000 RPM. The total assembly is maintained under reduced pressure at 60 mmHg abs to 250 mm Hg abs, preferably within 100 to 200 mm Hg abs. High agitator speed and hot surface of ATFE enable the acrylonitrile product to get quickly evaporated from the contaminated feed within a very short residence time living behind a residue of various contaminants. The product vapor is immediately evacuated into a condenser (4) where it is condensed at low temperature by chilled water, and collected in the receiver (5). Alternatively this vapor can be fed to an extractive distillation column for contacting with hydrophilic agents so as to reduce the moisture content to a desirable extent. The residue of acidic contaminants which contains only traces of acrylonitrile, is continuously withdrawn from the bottom of ATFE and can be safely disposed by conventional treatment methods. The purified acrylonitrile product removed from the upper portions of the distillation tower contains negligible amounts of contaminants such as residual acids and acrylamides and its moisture content is also substantially reduced.

The fresh acrylonitrile of commercial grade contains about 0.5% [by wt] of moisture in dissolved state. If this acrylonitrile is directly used as an excess reactant in the manufacture of materials such as 2-acrylamido-2-methyl propane sulfonic acid, it has been found that yield and selectivity drastically reduces. Therefore it is necessary to reduce the moisture content below 0.25 [by wt]. The inventors of this invention have developed an extractive distillation process for reducing the moisture content of acrylonitrile.

Now referring to FIG. 2, fresh acrylonitrile containing about 0.5% to 1% [by wt] of moisture as $H_2O$ is sucked by vacuum from container (3) into a 2 liter capacity three neck round bottom flask (7) which is immersed in a water bath (6) is heated by a heater (4). The round bottom flask (6) is filled with about 400 to 800 g and preferably about 500 to 700 g of hydrophilic agent and maintained at about 65 to 78° C., preferably at about 70 to 75° C., before the feed of acrylonitrile is made on. The feed rate of acrylonitrile is maintained at about 3 to 6 g/min, preferably at about 4 to 5 g/min. The flask (6) is connected to first packed section (8) of a distillation column of 25 mm diameter and 1100 mm height, packed with 10 mm glass bids. The top of this section is connected to a receiver (9) where the hydrophilic agent having moisture content less than 4000 ppm, preferably about 0 to 3000 ppm is sucked under vacuum via a dip tube from container (1). Container (1) is kept on a weighing scale (2) for cumulative weight measurement. The feed rate of hydrophilic agent is controlled with respect to that of fresh acrylonitrile in a ratio of about 0.5 to 2, preferably about 0.9 to 1.5. Receiver (9) is further connected to second packed section 10 of the distillation column of 25 mm diameter and 500 mm height, packed with 10 mm glass bids. The distillation column is provided with a condenser (14) via a vapor space (12). The condenser is conventionally provided with a circulation of chilled brine of suitable lower temperature. The distillate is collected in the receiver (11). Whole set up is maintained under reduced pressure at about 100 to 250 mmHg abs, preferably about 150 to 180 mmHg abs via the trap (13) and vacuum pump (5). The purified acrylonitrile product removed from the upper portions of the distillation tower contains negligible amount of moisture.

If the methods of this invention are followed, then acrylonitrile of very low water content and high purity, which is almost free from all the acidic contaminants generated during the synthesis of materials like 2-acrylamido-2-methyl propane sulfonic acid can be obtained. It is also found that the loss of acrylonitrile product due to polymerization is minimized by the method of present invention. Similarly the methods of this invention obviates the pretreatment of contaminated acrylonitrile by bases and thus the difficulties thereof and generates a residue which can be safely neutralized and disposed.

The novelty of the present invention lies in the purification of waste stream type contaminated acrylonitrile by avoiding polymerization of the acrylonitrile during purification and also purifying the contaminated acrylonitrile as well as fresh acrylonitrile having high moisture content by using hydrophilic agents, which make this process of purification economical and efficient.

The process of the present invention is described below with illustrative examples which should not be construed to limit the scope of the present invention in any manner.

EXAMPLE-1

Using Pilot Plant as Shown in FIG. 1

The agitated thin film evaporator [ATFE] (3) as indicated in FIG. 1 was provided with a zero clearance agitator. The agitator speed was 800 RPM. The heat transfer area was 0.12 square meter. The jacket was provided with hot oil circulation. The distillate condenser was provided with ice water circulation. The contaminated acrylonitrile from (1) was fed to (3) by pump (2) at a rate of 10.5 kg/h. ATFE was maintained at 140° C. Total assembly was maintained under reduced pressure at 200 mm Hg abs, The product vapor was immediately evacuated into condenser (4) where it was condensed at low temperature by ice-chilled water, and collected in receiver (5). Operation was carried out at steady state for 1 hour. Temperature of the vapor exiting from (3) was 45° C. Residue temperature was 88° C. Residue on analysis showed 8900 ppm of Acrylonitrile and 3.4% as water content. Moisture content in distillate was found to be 4000 ppm, while acidity as sulfuric acid was 0.12% by weight.

EXAMPLE-2

Using Pilot Plant as Shown in FIG. 1

The agitated thin film evaporator [ATFE] (3) as indicated in FIG. 1 was provided with a zero clearance agitator. The agitator speed was 800 RPM. The heat transfer area was 0.12 square meter. The jacket was provided with hot oil circulation. The distillate condenser was provided with ice water circulation. The contaminated acrylonitrile from (1) was fed to (3) by pump (2) at a rate of 10.5 kg/h. The ATFE was maintained at 140° C. The total assembly was maintained under reduced pressure at 170 mm Hg abs, The product vapor was immediately evacuated into condenser (4) where it was condensed at low temperature by ice-chilled water, and collected in the receiver (5). The operation was carried out at steady state for 1 hour. Temperature of the vapor exiting from (3) was 43° C. The residue temperature was 92° C. The residue on analysis showed 9400 ppm of Acrylonitrile content Moisture content in distillate was found to be 3000 ppm, while acidity as sulfuric acid was 0.13% by weight.

EXAMPLE-3

Using Pilot Plant as Shown in FIG. 1

The agitated thin film evaporator [ATFE] (3) as indicated in FIG. 1 was provided with a zero clearance agitator. The agitator speed was 800 RPM. The heat transfer area was 0.12 square meter. The jacket was provided with hot oil circulation. The distillate condenser was provided with ice water circulation. The contaminated acrylonitrile from (1) was fed to (3) by pump (2) at a rate of 10.5 kg/h. The ATFE was maintained at 146° C. The total assembly was maintained under reduced pressure at 200 mm Hg abs, The product vapor was immediately evacuated into condenser (4) where it was condensed at low temperature by ice-chilled water, and collected in the receiver (5). The operation was carried out at steady state for 1 hour. The temperature of the vapor exiting from (3) was 45° C. The residue temperature was 96° C. The residue on analysis showed 7300 ppm of Acrylonitrile content and 5.98% water by weight. The moisture content in distillate was found to be 2800 ppm, while the acidity as sulfuric acid was 0.11% by weight.

EXAMPLE-4

Using Pilot Plant as Shown in FIG. 1

Agitated thin film evaporator [ATFE] (3) as indicated in FIG. 1 was provided with a zero clearance agitator. Agitator speed was 800 RPM. Heat transfer area was 0.12 square meter. Jacket was provided with hot oil circulation. The distillate condenser was provided with ice water circulation. The contaminated acrylonitrile from (1) was fed to (3) by pump (2) at a rate of 10.5 kg/h. The ATFE was maintained at 120° C. The total assembly was maintained under reduced pressure at 100 mm Hg abs, The product vapor was immediately evacuated into condenser (4) where it was condensed at low temperature by ice-chilled water, and collected in the receiver (5). The operation was carried out at steady state for 1 hour. The temperature of the vapor exiting from (3) was 42° C. the residue temperature was 92° C. The residue on analysis showed 6976 ppm of Acrylonitrile content The moisture content in distillate was found to be 3000 ppm while the acidity as sulfuric acid, was 0.09% by weight.

EXAMPLE-5

Using Experimental Set-Up as Shown in FIG. 2

Fresh acrylonitrile of commercial grade containing 1.0042% [by wt] of moisture in dissolved state was continuously fed from container (3) into the 2 liter capacity three neck round bottom flask (7) which was immersed in a water bath (6) and heated by a heater (4). The round bottom flask (6) was filled with 600 g 1,2-propylene glycol having a moisture content of 2937 ppm [by wt.] and was maintained at 70° C. before the feed of acrylonitrile was made on. The feed rate of acrylonitrile was maintained at 5 g/min. The flask (6) was connected to first packed section (8) of the distillation column of 25 mm diameter and 1100 mm height, packed with 10 mm glass bids. The top of this section was connected to a receiver (9) where 1,2-propylene glycol having a moisture content of 2937 ppm was is sucked under vacuum via a dip tube from container (1). Container (1) was kept on a weighing scale (2) for cumulative weight measurement. The feed rate of 1,2-propylene glycol was controlled with respect to that of fresh acrylonitrile in a ratio of about 1.0. Receiver (9) was further connected to second packed section (10) of the distillation column of 25 mm diameter and 500 mm height, packed with 10 mm glass bids. The distillation column was provided with a condenser (14) via a vapor space (12). The condenser was conventionally provided with a circulation of chilled brine of suitable lower temperature. The distillate was collected in the receiver (11). Whole set up was maintained under reduced pressure at 172 mmHg abs, via the trap (13) and vacuum pump (5). The purified acrylonitrile product removed from the upper portions of the distillation tower was analysed for moisture content by Karl-Fischer titration method and was found to be 2060 ppm [ by wt].

EXAMPLE-6

Using Experimental Set-Up as Shown in FIG. 2

Fresh acrylonitrile of commercial grade containing 1.0042% [by wt] of moisture in dissolved state was continuously fed from container (3) into the 2 liter capacity three neck round bottom flask (7) which was immersed in a water bath (6) and heated by a heater (4). The round bottom flask (6) was filled with 600 g 1,2-propylene glycol having a moisture content of 2937 ppm [by wt] and was maintained at 70° C. before the feed of acrylonitrile was made on. Feed rate of acrylonitrile was maintained at 5 g/min. Flask (6) was connected to first packed section (8) of a distillation column of 25 mm diameter and 1100 mm height, packed with 10 mm glass bids. Top of this section was connected to a receiver (9) where 1,2-propylene glycol having a moisture content of 2937 ppm was is sucked under vacuum via a dip tube from container (1). Container (1) was kept on a weighing scale (2) for cumulative weight measurement. Feed rate of 1,2-propylene glycol was controlled with respect to that of fresh acrylonitrile in a ratio of 1.15. Receiver (9) was further connected to second packed section (10) of the distillation column of 25 mm diameter and 500 mm height, packed with 10 mm glass bids. Distillation column was provided with a condenser (14) via a vapor space (12). Condenser was conventionally provided with a circulation of chilled brine of suitable lower temperature. Distillate was collected in the receiver (11). Whole set up was maintained under reduced pressure at 165 mmHg abs, via the trap (13) and vacuum pump (5). Purified acrylonitrile product removed from the upper portions of the distillation tower was analyzed for moisture content by Karl-Fischer titration method and was found to be 2000 ppm [ by wt].

EXAMPLE-7

Using Experimental Set-Up as Shown in FIG. 2

The fresh acrylonitrile of commercial grade containing 1.0042% [by wt] of moisture in dissolved state was continuously fed from container (3) into the 2 liter capacity three neck round bottom flask (7) which was immersed in a water bath (6) and heated by a heater (4). The round bottom flask (6) was filled with 600 g 1,2-propylene glycol having a moisture content of 2937 ppm [by wt.] and was maintained at 70° C. before the feed of acrylonitrile was made on. The feed rate of acrylonitrile was maintained at 5 g/min. The flask (6) was connected to first packed section (8) of a distillation column of 25 mm diameter and 1100 mm height, packed with 10 mm glass bids. The top of this section was connected to a receiver (9) where 1,2-propylene glycol having a moisture content of 2937 ppm was is sucked under vacuum via a dip tube from container (1). Container (1) was kept on a weighing scale (2) for cumulative weight measurement. The feed rate of 1,2-propylene glycol was controlled with respect to that of fresh acrylonitrile in a ratio of about 1.3. Receiver (9) was further connected to second packed section (10) of the distillation column of 25 mm diameter and 500 mm height, packed with 10 mm glass bids. The distillation column was provided with a condenser (14) via a vapor space (12). The condenser was conventionally provided with a circulation of chilled brine of suitable lower temperature. The distillate was collected in the receiver (11). Whole set up was maintained under reduced pressure at 168 mmHg abs, via the trap (13) and vacuum pump (5). The purified acrylonitrile product removed from the upper portions of the distillation tower was analyzed for moisture content by Karl-Fischer titration method and was found to be 1970 ppm [ by wt].

Advantages of the Invention

1. From the foregoing examples it can be seen that the method of quick evaporation of the contaminated acrylonitrile and that of extractive distillation of fresh acrylonitrile by countercurrent contacting with a hydrophilic agent as disclosed by this invention can be suitably combined to give very good quality acrylonitrile which can be reused in the processes where excess acrylonitrile is used such as that in the production of materials like 2-acrylamido-2-methyl propane sulfonic acid.

2. An important advantage of this invention is that it allows for the purification of such waste stream type contaminated acrylonitrile while avoiding polymerization of the acrylonitrile during purification 3. The present invention provides a method for purifying acrylonitrile which uses quick vaporizing devices, hydrophilic agents, vacuum and while being economical and efficient.

4. The present invention provides a method for purifying acrylonitrile, which is environmentally acceptable, and in compliance with environmental laws.

5. It also provides an acrylonitrile purification process, which reduces the build up of deposits on equipment in that polymerization is reduced greatly and salts formed are removed early in processing.

An important feature of the present invention is that it provides a means whereby unreacted acrylonitrile used in the production of 2-acrylamido-2-methyl propane sulfonic acid can be reused to produce a purified product such as 2-acrylamido-2-methyl propane sulfonic acid having the desired characteristics such as storage stability and the lack of high molecular weight water insoluble polymers formed by the reaction of acrylonitrile with various reactive contaminants.

We claim:

1. A process for the recovery of acrylonitrile from contaminated acrylonitrile or fresh acrylonitrile having 0.5–1% moisture content or a mixture thereof in a waste stream, the process consisting of:
   (a) vaporizing the contaminated acrylonitrile or fresh acrylonitrile having 0.5–1% moisture content or a mixture thereof in an agitated thin film evaporator (ATFE) running at a speed of 600–1200 rpm, at a temperature of 100–150° C. under reduced pressure of 60–250 mm Hg abs, to obtain a vapor feed;
   (b) contacting the vapor feed so obtained with a hydrophilic agent; and
   (c) condensing the contacted vapor feed to obtain the desired acrylonitrile.

2. A process as claimed in claim 1, wherein the speed of the agitated thin film evaporator (ATFE) used is in the range of 700–1000 rpm.

3. A process as claimed in claims 1, wherein the temperature used for vaporizing is in the range of 120–140° C.

4. A process as claimed in claim 1, wherein the reduced pressure used is in the range of 100–200 mmHg abs.

5. A process as claimed in claim 1, wherein the hydrophillic agent used is a compound having a diol group.

6. A process as claimed in claim 5 wherein the hydrophilic agent is selected from the group consisting of 1,2-Propane Diol, mono ethylene glycol, Di-ethylene glycol and glycerol.

* * * * *